United States Patent
Hu et al.

(10) Patent No.: US 10,839,962 B2
(45) Date of Patent: Nov. 17, 2020

(54) SYSTEM, METHOD AND COMPUTER PROGRAM PRODUCT FOR EVALUATION AND IDENTIFICATION OF RISK FACTOR

(71) Applicant: International Business Machines Corporation, Armonk, NY (US)

(72) Inventors: Gang Hu, Beijing (CN); Xiang Li, Beijing (CN); Haifeng Liu, Beijing (CN); Zhaonan Sun, Elmsford, NY (US); Jingjing Tao, Shanghai (CN); Guo Tong Xie, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 383 days.

(21) Appl. No.: 15/275,873

(22) Filed: Sep. 26, 2016

(65) Prior Publication Data
US 2018/0089389 A1    Mar. 29, 2018

(51) Int. Cl.
G16H 50/30 (2018.01)
G16H 50/50 (2018.01)
G16H 50/70 (2018.01)

(52) U.S. Cl.
CPC ............. *G16H 50/30* (2018.01); *G16H 50/50* (2018.01); *G16H 50/70* (2018.01)

(58) Field of Classification Search
CPC ......... G16H 50/30; G16H 50/50; G16H 50/70
See application file for complete search history.

(56) References Cited

U.S. PATENT DOCUMENTS

| 7,319,970 | B1 * | 1/2008 | Simone | G06F 19/328 |
| | | | | 705/4 |
| 8,758,243 | B2 * | 6/2014 | Wang | A61B 5/0402 |
| | | | | 600/301 |
| 2002/0159641 | A1 * | 10/2002 | Whitney | G06K 9/6228 |
| | | | | 382/219 |

(Continued)

FOREIGN PATENT DOCUMENTS

WO    WO-2004075010 A2 *    9/2004    ............. G16B 20/00

OTHER PUBLICATIONS

"Cox proportional-hazards regression" website printout, archied on Nov. 25, 2010, 4 pages (Year: 2010).*

(Continued)

*Primary Examiner* — Aryan E Weisenfeld
*Assistant Examiner* — Steven G Sanghera
(74) *Attorney, Agent, or Firm* — Joseph Petrokaitis, Esq.; McGinn IP Law Group, PLLC

(57) ABSTRACT

A method, system, and computer program product, include obtaining a plurality of training sets of samples and a plurality of testing sets of samples from a data set of clinical records, the plurality of training sets of samples and the corresponding plurality of testing sets of samples including different samples of the data set, determining statistical significance for a plurality of risk factors of a model from the plurality of training sets of samples, determining a plurality of performance metrics of the model from the plurality of testing sets of samples, and determining an evaluation metric of the plurality of risk factors for the model based on the statistical significance and the plurality of performance metrics, the evaluation metric being for improving accuracy of the model.

12 Claims, 6 Drawing Sheets

(56) References Cited

U.S. PATENT DOCUMENTS

| | | | | |
|---|---|---|---|---|
| 2003/0005180 A1* | 1/2003 | Schmit | ............... | G06F 8/71 719/328 |
| 2005/0021236 A1 | 1/2005 | Aston et al. | | |
| 2005/0032066 A1 | 2/2005 | Heng et al. | | |
| 2007/0016542 A1* | 1/2007 | Rosauer | ............ | G06N 5/022 706/21 |
| 2011/0137131 A1* | 6/2011 | Adourian | ......... | G01N 33/6893 600/300 |
| 2013/0102867 A1* | 4/2013 | Desborough | ....... | A61B 5/7225 600/365 |
| 2014/0095184 A1 | 4/2014 | Gotz et al. | | |

OTHER PUBLICATIONS

"How to compute p-values and Cohen's d for z-tests" website printout, archived on Sep. 6, 2015, 3 pages (Year: 2015).*

Michael J. Pencina et al., "Evaluating the added predictive ability of a new marker: From are under the ROC curve to reclassification and beyond" website printout, 2008, 16 pages (Year: 2008).*

"Beginners statistics: proportions" website printout, archived on Jul. 30, 2016, 1 page (Year: 2016).*

"How to compute p-values and Cohen's d for tests" website printout, archived on Sep. 6, 2015, 3 pages (2 copies, 1 with the archive date and 1 of the entire document) (Year: 2015).*

Michael J. Pencina et al., "Evaluating the added predictive ability of a new marker: From area under the ROC curve to reclassification and beyond" website printout, 2008, 16 pages (Year: 2008).*

"Cox proportional-hazards regression" website printout, archived on Nov. 25, 2010, 4 pages (Year: 2010).*

Mel, et al. "The NIST Definition of Cloud Computing". Recommendations of the National Institute of Standards and Technology. Nov. 16, 2015.

Diaz-Diaz, Norberto, et al. "Feature selection based on bootstrapping". BIGA, BioInformatics Group Seville. University of Seville, Spain. IEEE, 2005.

Khan, Mehnaz, et al. "Effects of Using Filter Based Feature Selection on the Performance of Machine Learners Using Different Datasets". BIJIT—BVICAM's International Journal of Information Technology. Aug. 2013.

Matheny, M.E. et al. "Discrimination and calibration of mortality risk prediction models in interventional cardiology". Journal of Biomedical Informatics. Mar. 26, 2005.

* cited by examiner

SYSTEM, METHOD AND COMPUTER PROGRAM PRODUCT FOR EVALUATION AND IDENTIFICATION OF RISK FACTOR

BACKGROUND

The present invention relates generally to a risk evaluation method, and more particularly, but not by way of limitation, to a system, method, and computer program product for evaluating a subset of risk factors so as to identify optimal risk factors.

As more clinical information with increasing diversity becomes available for analysis, a large number of features or risk factors can be constructed and leveraged for predictive modeling. As used herein, a risk factor refers to any attribute, characteristic or exposure of an individual that increases the likelihood of developing a disease or injury. Some examples of the more important risk factors are underweight, unsafe sex, high blood pressure, tobacco and alcohol consumption, and unsafe water, sanitation and hygiene. The ability to identify risk factors related to an adverse health condition (for example, congestive heart failure) is very important for improving healthcare quality and reducing cost. The identification of risk factors may allow for the early detection of the onset of diseases so that aggressive intervention may be taken to slow or prevent costly and potentially life threatening conditions.

SUMMARY

In an exemplary embodiment, the present invention can provide a computer-implemented method including obtaining a plurality of training sets of samples and a plurality of testing sets of samples from a data set of clinical records, the plurality of training sets of samples and the corresponding plurality of testing sets of samples including different samples of the data set, determining statistical significance for a plurality of risk factors of a model from the plurality of training sets of samples, determining a plurality of performance metrics of the model from the plurality of testing sets of samples, and determining an evaluation metric of the plurality of risk factors for the model based on the statistical significance and the plurality of performance metrics, the evaluation metric being for improving accuracy of the model.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
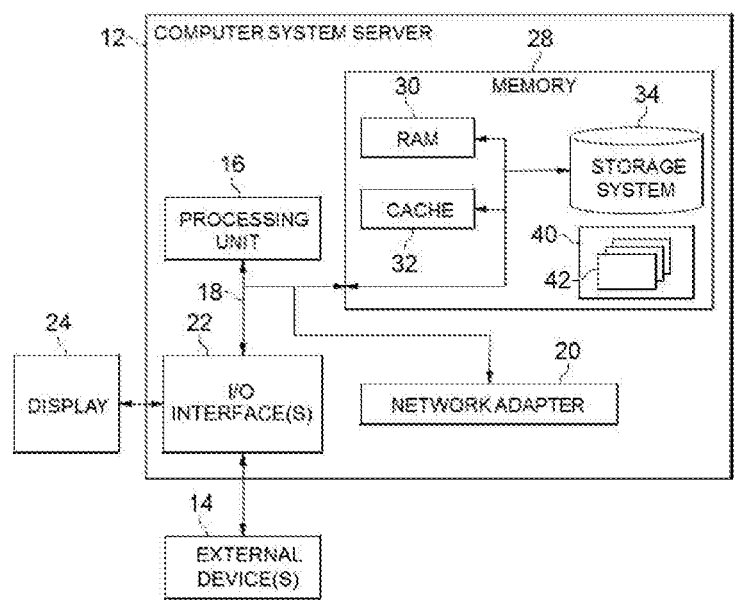
FIG. 1 depicts a cloud computing node 10 according to an embodiment of the present invention.

The invention will now be described with reference to FIG. 1-7, in which like reference numerals refer to like parts throughout. It is emphasized that, according to common practice, the various features of the drawing are not necessarily to scale. On the contrary, the dimensions of the various features can be arbitrarily expanded or reduced for clarity.

Figure 5:
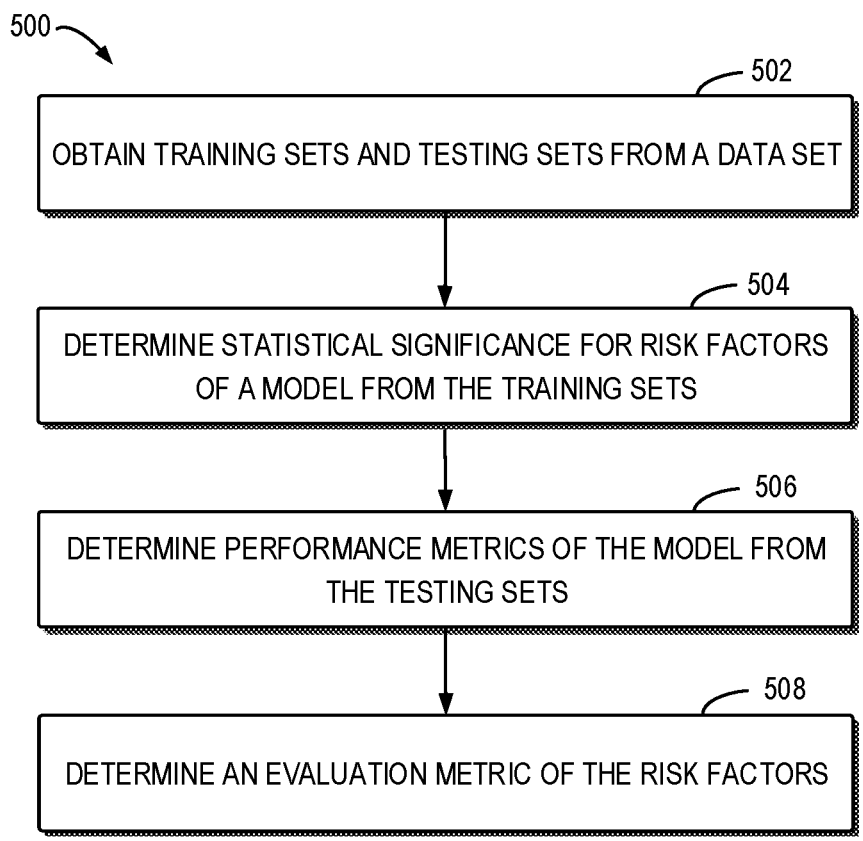
FIG. 5 is a flowchart of a process for evaluating risk factors of a risk prediction model in accordance with embodiments of the present disclosure.

With reference now to the example depicted in FIG. 5, the method 500 includes various steps to determine an evaluation metric of the plurality of risk factors for the model based on the statistical significance and the plurality of performance metrics. As shown in at least FIG. 1, one or more computers of a computer system 12 according to an embodiment of the present invention can include a memory 28 having instructions stored in a storage system to perform the steps of FIG. 5.

Although one or more embodiments (see e.g., FIGS. 1 and 6-7) may be implemented in a cloud environment 50 (see e.g., FIG. 6), it is nonetheless understood that the present invention can be implemented outside of the cloud environment.

Risk prediction models typically use a number of risk factors based on patient characteristics to predict health outcomes. Such models are a cornerstone of modern clinical medicine. For example, the models are often used to predict the probability that an individual with a given set of risk factors will experience a health outcome. The risk prediction models can help in clinical decision making and help patients make an informed choice regarding their treatment. The risk models are usually developed using several risk factors typically based on patient characteristics that are thought to be associated with the health event of interest. Given patient characteristics, the risk model can calculate the probability of a patient having the health outcome.

The risk prediction models typically take advantage of a generalized linear model (GLM), for example, a logistic regression model. The risk factors, also referred to as features of a model, are usually selected based on the statistical significance of each risk factor and the prediction performance of the model. Statistical significance (or a statistically significant result) is attained if a p-value is less than the significance level. The p-value is the probability of obtaining at least as extreme results given that the null hypothesis is true whereas the significance level is the probability of rejecting the null hypothesis given that it is true. The prediction performance of the model may be evaluated by a number of measures, in which a very common one is Area Under the receiver operating characteristic (ROC) Curve (AUC). The ROC curve is a graphical plot that illustrates the performance of a binary classifier as its discrimination threshold is varied.

Conventionally, the feature selection methods can only optimize at most one of the above two aspects. As a result, the risk factors as selected in accordance with one aspect are usually unsatisfactory in terms of the other aspect. Embodiments of the present disclosure can at least in part solve this problem and potentially other problems.

Figure 2:
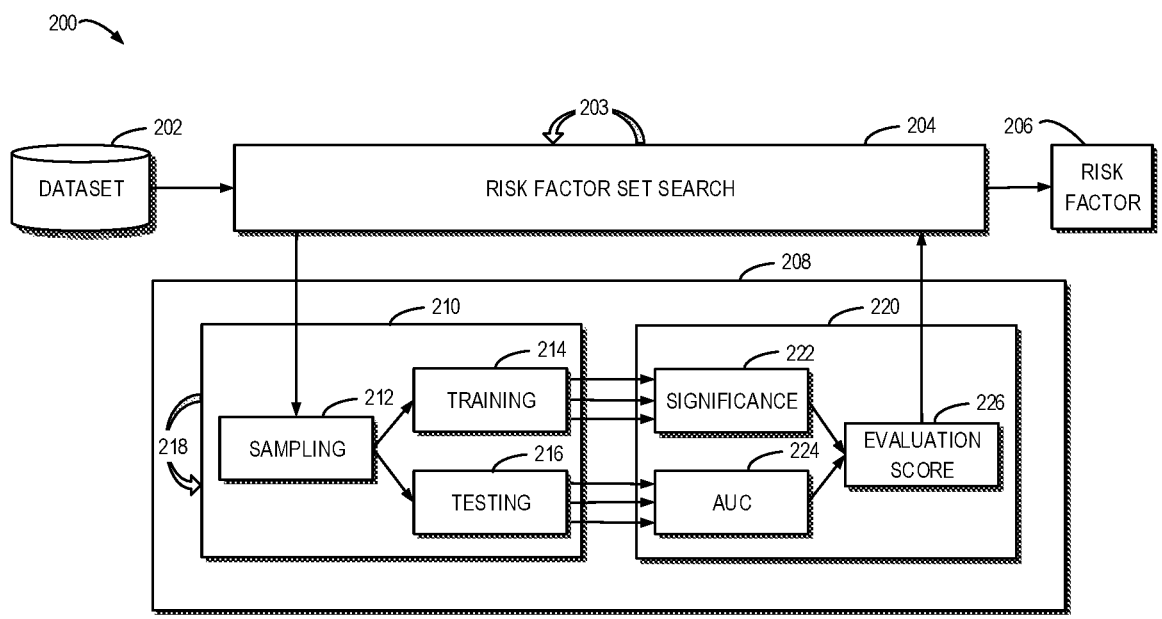
FIG. 2 is a block diagram illustrating a system for identifying risk factors in accordance with embodiments of the present disclosure.

FIG. 2 shows a high-level block diagram showing a system 200 for identifying risk factors. As shown, the data set 202 may include clinical information of various individuals, for example, clinical records. The data set 202 may be stored in the storage system 34 as shown in FIG. 1. The search engine 204 may store a set of risk factors, or optionally receive the set of risk factors from the storage system 34, for example. In operation, the search engine 204 may iteratively search the risk factor set as indicated by the arrow 203 and determine multiple subsets of risk factors and provide each subset of risk factors to the modeling block 210, in particular the sampling block 212. The modeling block 210 may determine an evaluation metric for each subset of risk factors and provide the metrics back to the search engine 204. The search engine 204 may then compare the evaluation metrics and determine an optimal subset of risk factors 206. In some embodiments, the evaluation metric may be embodied as an evaluation score, for example.

In accordance with embodiments of the present disclosure, the evaluation scores of the subsets of risk factors may be determined by the block 208 on the basis of both the statistical significance of the risk factors and the predictive power of the model. Statistical significance may indicate that whether the associated risk factor is occasional or statistically significant. The sampling block 212 also obtains multiple subsets of data samples from the data set 202. For example, the sampling block 212 may simply divide the data set 202 into multiple subsets.

The data samples in each subset are not necessarily different and may be duplicated because clinical data are generally difficult to collect and the size of the data set 202 may be limited. For example, the sampling block 212 may obtain multiple subsets of data samples by a bootstrapping method. Bootstrapping relies on random sampling with replacement and falls in the broader class of resampling methods. The bootstrapping method is described only for the purpose of illustration without suggesting any limitation as to the scope of the disclosure.

Figure 3:
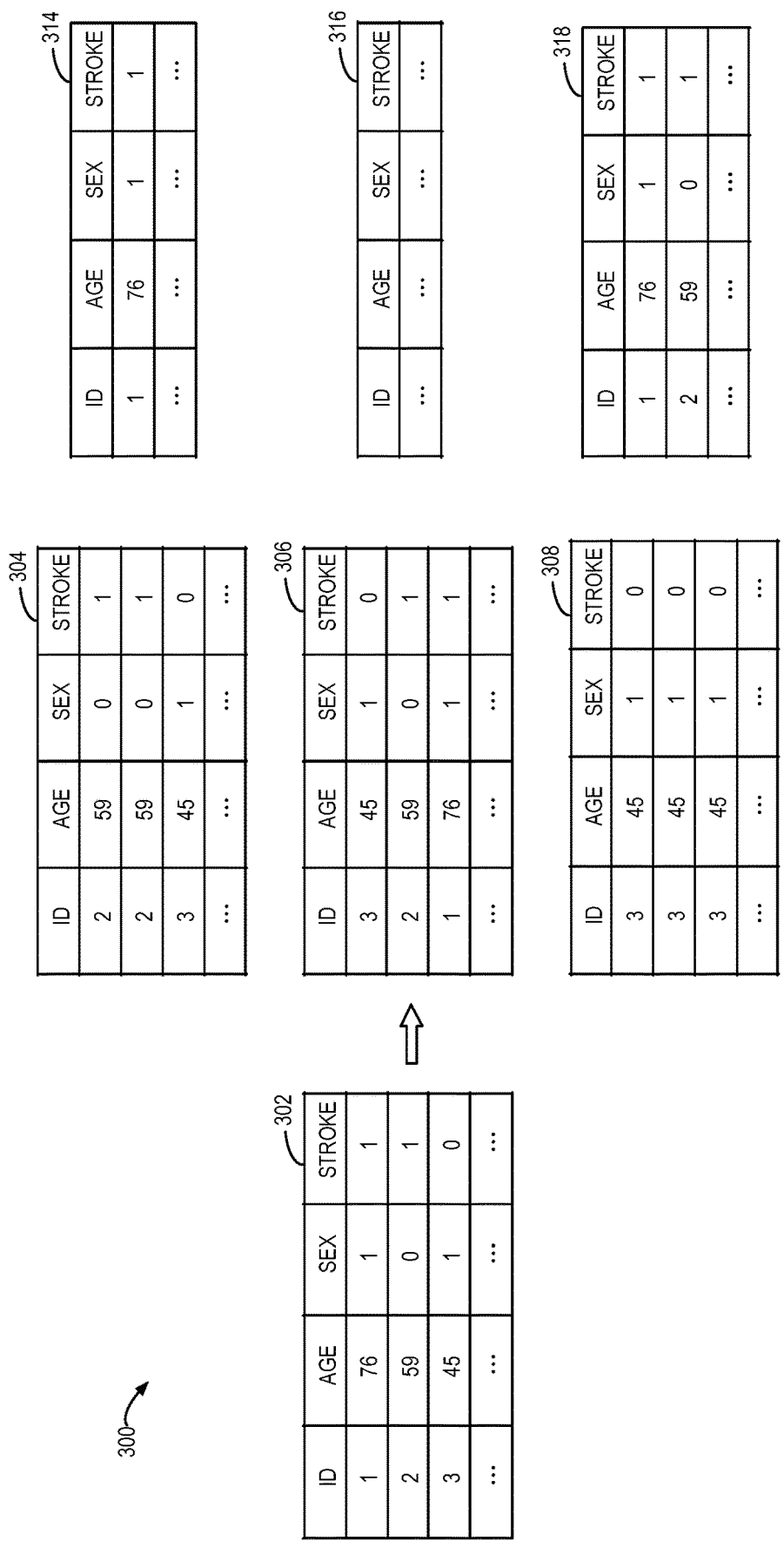
FIG. 3 is a schematic diagram illustrating a sampling process in accordance with embodiments of the present disclosure.

FIG. 3 is a schematic diagram 300 showing the bootstrapping method performed by the sampling block 212. In this example, the data set 302 includes four entries, ID, age, sex, and stroke, in which age and sex are two risk factors. In other words, in the shown example, the feature subset includes age and sex. The stroke entry indicates the possible outcome, with the value 0 indicating an outcome of no stroke and the value 1 indicating an outcome of stroke.

In some embodiments, the data set 302 may be sampled by bootstrapping to obtain a set of data samples 304, which may be also referred to as training sets 304 or a set of bootstrap samples 304. Accordingly, a set of data samples 314, also referred to as testing set 314, may be selected or otherwise determined from the data samples in the data set 302 but not in the training set 304. In other words, instances that are not sampled into the training set 304 may be selected into the testing set 314. In some embodiments, the testing set 314 includes all the data samples that are in the data set 302 but not in the training set 304.

The bootstrapping method may be repeated iteratively as indicated by the arrow 218 to obtain multiple training sets and respective testing sets. For example, a training set 306 may be obtained by sampling the data set 302 and a testing set 316 may be determined from the data samples in the data set 302 but not in the training set 306. A training set 308 may be obtained by sampling the data set 302 and a testing set 318 may be determined from the data samples in the data set 302 but not in the training set 308. As described above, the bootstrapping method is a resampling method and thus the bootstrap samples may be duplicated.

Referring back to FIG. 2, the training block 214 may receive multiple training sets (for example, training sets 304, 306, and 308) from the sampling block 212 and train a predictive model from each training set to obtain a set of coefficients of risk factors. The testing block 216 may receive from the training block 214 the predictive model, for example, the coefficients of risk factors, and then determine the respective performance (for example, AUC) of the predictive model through respective testing set. It is to be understood that the performance metric AUC is described only for the purpose of illustration without suggesting any limitation as to the scope of the disclosure. The disclosure herein can be implemented by means of any performance metric currently known or to be developed in the future.

Figure 4:
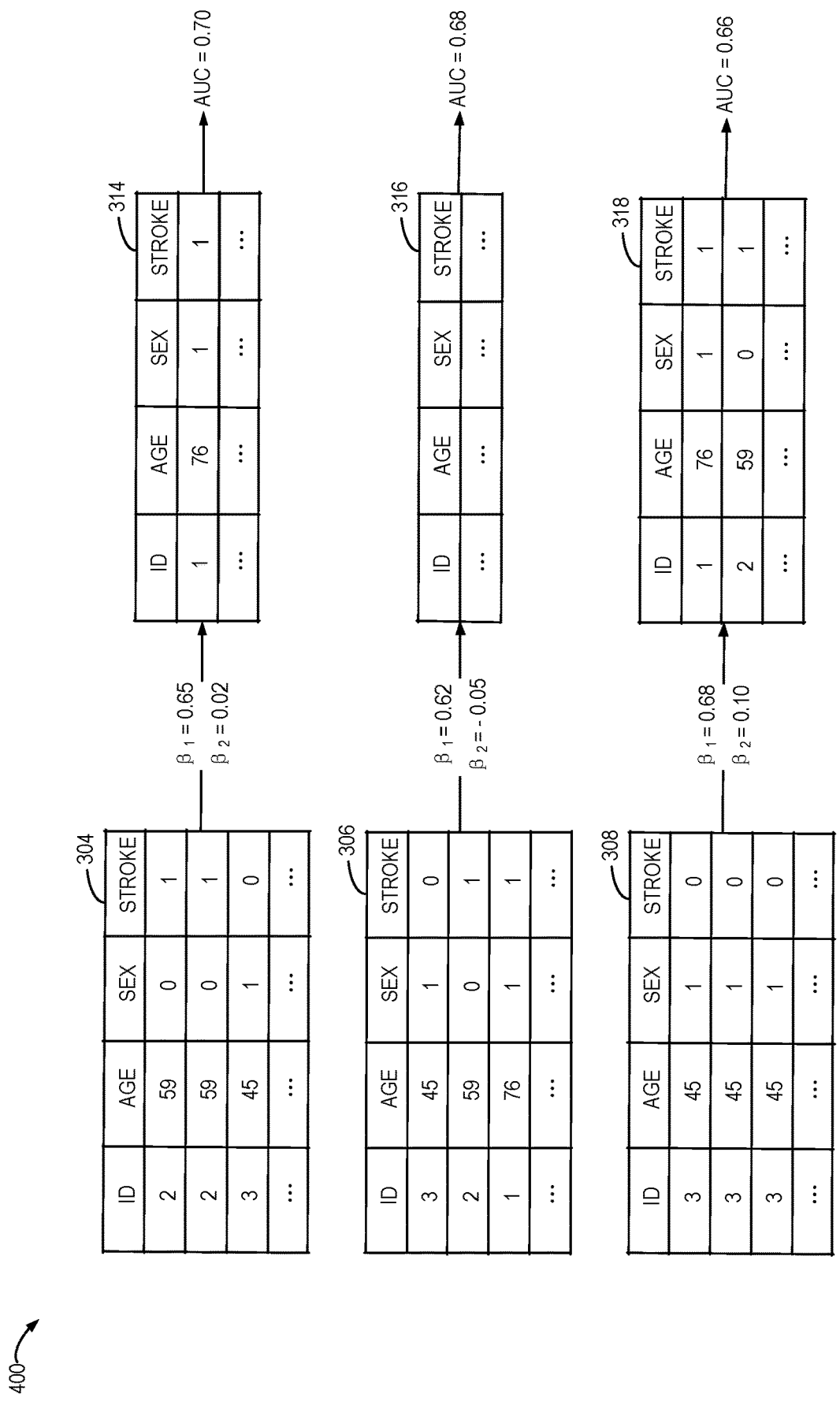
FIG. 4 is a schematic diagram illustrating training and testing processes in accordance with embodiments of the present disclosure.

Referring now to FIG. 4, a schematic diagram 400 showing the training and testing processes performed by the blocks 214 and 216 is illustrated. By way of example, a logistic regression model may be expressed by the equation $y=\text{logistic}(\beta_0+\beta_1 x_1+\beta_2 x_2)$, where y represents the outcome of stroke, with 0 indicating the outcome of no stroke and 1 indicating the outcome of stroke, $x_1$ and $x_2$ represents risk factors, for example, age and sex of the individuals, the coefficient $\beta_0$ represents an intercept term, and the coefficients $\beta_1$ and $\beta_2$ are directed to their respective risk factors.

As shown in FIG. 4, a set of coefficients may be determined from each training set 304, 306, or 308. For example, the coefficients $\beta_1=0.65$ and $\beta_2=0.02$ are determined from the training set 304 and provided to the testing block 216 to evaluate the AUC of the logistic regression model, which turns out to be 0.70. Likewise, the coefficients $\beta_1=0.62$ and $\beta_2=-0.05$ are determined from the training set 306 and provided to the testing block 216 to evaluate the AUC of the model based on the testing set 316, which turns out to be 0.68. The coefficients $\beta_1=0.68$ and $\beta_2=0.10$ are determined from the training set 308 and provided to the testing block 216 to evaluate the AUC of the model based on the testing set 318, which turns to be 0.66. For the sake of clarity, the values of the coefficient $\beta_0$ have been omitted herein.

Still in reference to FIG. 2, the statistics block 222 in the evaluation block 220 receives multiple sets of coefficients from the training block 214 and determines the statistical significance for each risk factor. For example, a p-value for a risk factor may be determined based on the mean $\bar{\beta}_l$ and standard error $\sigma_l$ of the coefficients of each risk factor l from the training sets. The p-values $p_l$ of each risk factor l may be determined by performing z-test: $p_l=\text{Prob}(z \geq \bar{\beta}_l/\sigma_l)$, where $\text{Prob}(z \geq \bar{\beta}_l/\sigma_l)$ represents the probability of the outcomes that satisfy the event $z \geq \bar{\beta}_l/\sigma_l$. The z-test method is well-known in statistics, and thus the details thereof are omitted herein.

In this way, the mean and standard error of the coefficient $\beta_1$ may be determined as $\overline{\beta_1}=0.65$ and $\sigma_1=0.03$, and the p-value may then be determined as $p_1<0.001$. Similarly, the mean and standard error of the coefficient $\beta_2$ may be determined as $\overline{\beta_2}=0.023$, and $\sigma_2=0.075$, and the p-value may be then determined as $p_2=0374$.

The AUC block 224 receives multiple AUC values from the testing block 216 and determines the mean of AUC: $\overline{AUC}=0.68$. The evaluation score block 226 receives the statistical data from statistics block 222 and AUC block 224 and then determines an evaluation score s for the subset of risk factors by combining the p-values and AUC. As described above, the performance metric AUC is described only for the purpose of illustration, without suggesting any limitation as to the scope of the disclosure.

In some embodiments, the score s may be determined by favoring the prediction performance of the model and penalizing p-values of risk factors. In other words, the score s may increase as the prediction performance of the model increases while the score may decrease as the p-values of risk factors increase.

For example, the evaluation score s may be calculated by the equation:

$$s = \alpha \cdot \overline{AUC} + (1-\alpha)/k \cdot \Sigma_{j=1}^{k}(1-I(p_1>\theta) \cdot p_1),$$

where k represents the number of risk factors, $\alpha \in (0,1]$ represents a parameter to balance prediction performance and statistical significance, and $\theta$ represents a predefined threshold for p-value, also referred to as significance level, for example, 0.1, 0.05, or 0.01. The function $I(p_j>\theta)$ represents an indicator function, having the value 1 for all the p-values satisfying $p_j>\theta$ and the value 0 for all the p-values not satisfying $p_j>\theta$. By way of example, if $\alpha=0.9$ and $\theta=0.05$, the evaluation score s may be determined by $$s = 0.9 \cdot 0.68 + \frac{0.1}{2} \cdot ((1-0) + (1-1 \cdot 0.374)) = 0.693.$$

It is to be understood that evaluation score s is described only for purpose of illustration without suggesting any limitation as to the scope of the disclosure. The disclosure described herein can be implemented by means of any evaluation metric without departing from the scope of the present disclosure.

Feature selection can be seen as the combination of a search technique for proposing new feature subsets, along with an evaluation measure which scores the different feature subsets. The choice of evaluation metric heavily influences the feature selection process. In accordance with embodiments of the present disclosure, the evaluation metric (for example, the evaluation score s) takes into account of both the statistical significance of the features and the predictive power of the model.

As described above, the search engine 204 may implement a wrapper method to obtain different subsets of risk factors and then compare the evaluation scores of the subsets provided by the sampling and evaluation block 208 so as to determine an optimal subset of risk factors 206. The search process performed by the search engine 204 may be methodical such as a best-first search, it may be stochastic such as a random hill-climbing algorithm, or it may use heuristics, like forward and backward passes to add and remove features. It is to be understood that these embodiments are described only for the purpose of illustration and help those skilled in the art to understand and implement the present disclosure, without suggesting any limitations as to the scope of the disclosure.

For example, the search engine 204 may obtain another feature subset, including age, sex, and weight and provide the subset to the sampling and evaluation block 208 to obtain an evaluation score for the feature subset. The search engine 204 may compare the evaluation scores to determine an optimal feature subset. For example, the feature subset will become better as the evaluation score s increases.

FIG. 5 is a flow chart illustrating a process 500 of evaluating risk factors of a risk prediction model in accordance with embodiments of the present disclosure. The process 500 can be carried out by the sampling and evaluation block 208 and optionally the search engine 204 as shown in FIG. 2.

At 502, a plurality of training sets of samples and a plurality of testing sets of samples may be obtained from a data set of clinical records. The plurality of training sets of samples and the corresponding plurality of testing sets of samples include different samples of the data set. In some embodiments, the plurality of training sets of samples may be determined by performing a bootstrapping method on the data set. The plurality of testing sets of samples may be determined from samples that are not in the corresponding plurality of training sets of samples. The evaluation metric may be used to improve accuracy of the model.

At 504, statistical significance for a plurality of risk factors of a model may be determined from the plurality of training sets of samples. The model generates a prediction at least in part based on the plurality of risk factors. In some embodiments, a plurality of coefficients for the plurality of risk factors may be determined from the plurality of training sets of samples. A plurality of values indicating the statistical significance for the plurality of risk factors may be determined based on the plurality of coefficients. In some embodiments, means and standard errors of the plurality of coefficients for the plurality of risk factors may be determined and then a plurality of p-values may be determined based on the means and standard errors of the plurality of coefficients.

At 506, a plurality of performance metrics of the model may be determined from the plurality of testing sets of samples. In some embodiments, the performance metric may be area under the receiver operating characteristic (ROC) curve (AUC).

At 508, an evaluation metric of the plurality of risk factors for the model may be determined based on the statistical significance and the plurality of performance metrics.

In some embodiments, the evaluation metric may be determined by favoring the plurality of performance metrics and penalizing the p-values.

In some embodiments, a second plurality of training sets of samples and a second plurality of testing sets of samples may be obtained from the data set. The second plurality of training sets of samples and the corresponding second plurality of testing sets of samples include different samples of the data set. A second statistical significance for a second plurality of risk factors of a model may be determined from the second plurality of training sets of samples. A second plurality of performance metrics of the model may be determined from the second plurality of testing sets of samples. Then a second evaluation metric of the second plurality of risk factors for the model may be determined based on the second statistical significance and the plurality of performance metrics. In this way, one of the plurality of risk factors and the second plurality of risk factors may be determined as optimal risk factors based on the evaluation metric and the second evaluation metric.

Exemplary Aspects, Using a Cloud-Computing Environment

Although this detailed description includes an exemplary embodiment of the present invention in a cloud-computing environment, it is to be understood that implementation of the teachings recited herein are not limited to such a cloud-computing environment. Rather, embodiments of the present invention are capable of being implemented in conjunction with any other type of computing environment now known or later developed.

Cloud-computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud-computing environment is service oriented with a focus on statelessness, low coupling, modularity, and semantic interoperability. At the heart of cloud-computing is an infrastructure comprising a network of interconnected nodes.

Referring now to FIG. 1, a schematic of an example of a cloud-computing node is shown. Cloud-computing node 10 is only one example of a suitable node and is not intended to suggest any limitation as to the scope of use or functionality of embodiments of the invention described herein. Regardless, cloud-computing node 10 is capable of being implemented and/or performing any of the functionality set forth herein.

Although cloud-computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud-computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud-computing environments where tasks are performed by remote processing circuits that are linked through a communications network. In a distributed cloud-computing environment, program modules may be located in both local and remote computer system storage media including memory storage circuits.

Referring again to FIG. 1, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 6:
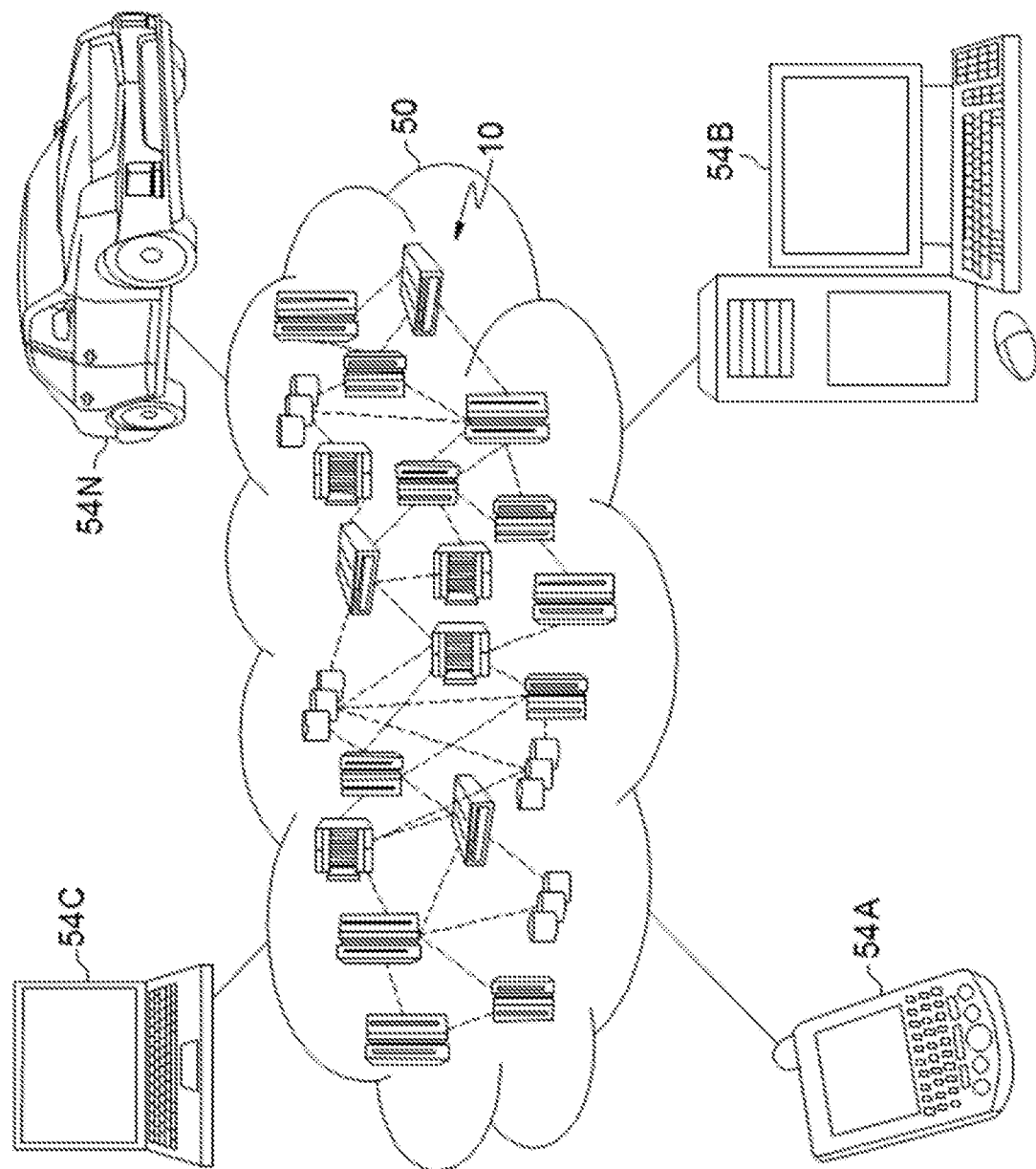
FIG. 6 depicts a cloud computing environment 50 according to an embodiment of the present invention.

Referring now to FIG. 6, illustrative cloud-computing environment 50 is depicted. As shown, cloud-computing environment 50 comprises one or more cloud-computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud-computing environment 50 to offer infrastructure, platforms and/or software as services for which a cloud consumer does not need to maintain resources on a local computing circuit. It is understood that the types of computing circuits 54A-N shown in FIG. 6 are intended to be illustrative only and that computing nodes 10 and cloud-computing environment 50 can communicate with any type of computerized circuit over any type of network and/or network addressable connection (e.g., using a web browser).

Figure 7:
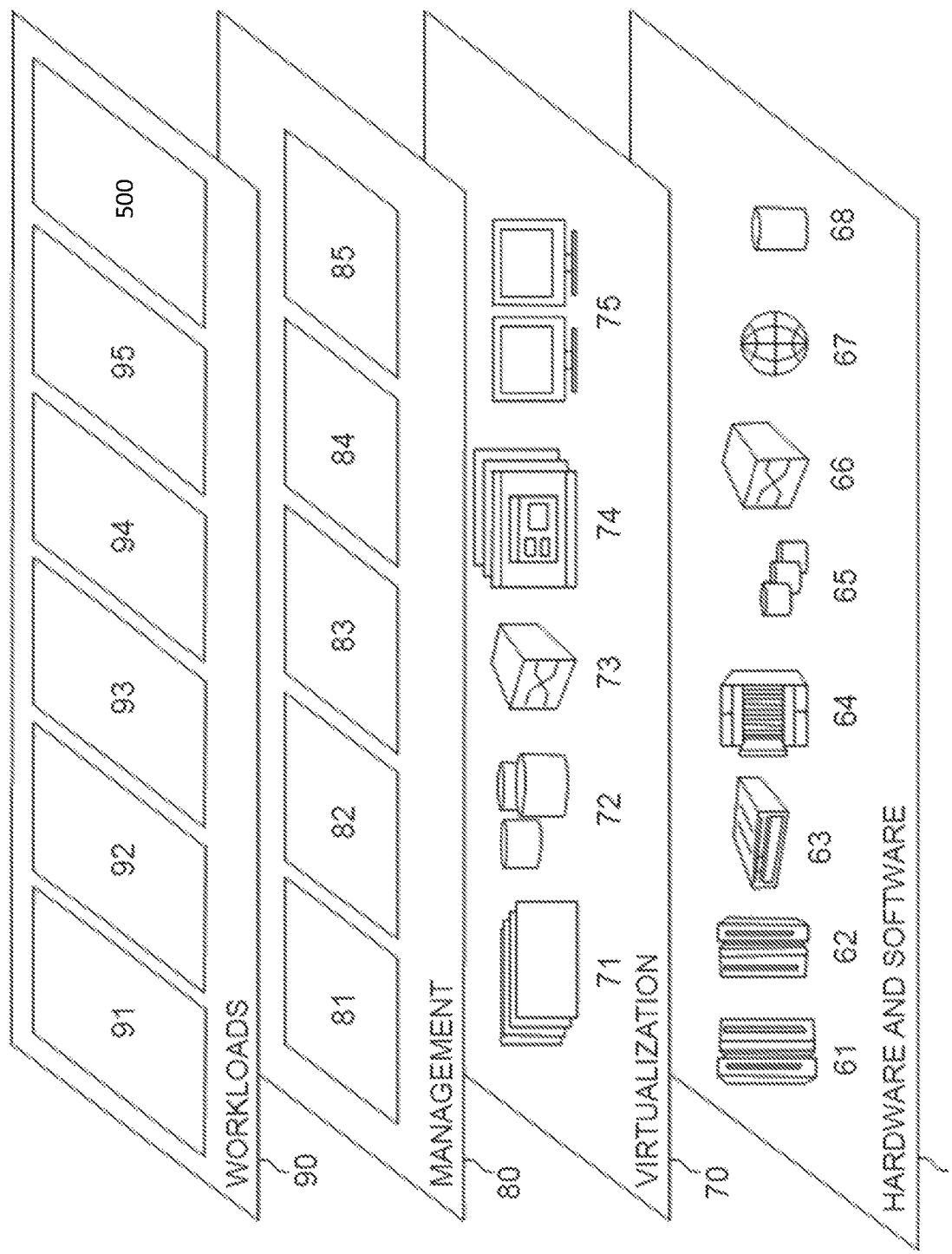
FIG. 7 depicts abstraction model layers according to an embodiment of the present invention.

Referring now to FIG. 7, an exemplary set of functional abstraction layers provided by cloud-computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud-computing environment. Metering and Pricing 82 provide cost tracking as resources are utilized within the cloud-computing environment, and billing or invoicing for consumption of these resources. In one example, these resources may comprise application software licenses. Security provides identity verification for cloud consumers and tasks, as well as protection for data and other resources. User portal 83 provides access to the cloud-computing environment for consumers and system administrators. Service level management 84 provides cloud-computing resource allocation and management such that required service levels are met. Service Level Agreement (SLA) planning and fulfillment 85 provide pre-arrangement for, and procurement of, cloud-computing resources for which a future requirement is anticipated in accordance with an SLA.

Workloads layer 90 provides examples of functionality for which the cloud-computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the method 500.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented method comprising:
obtaining a plurality of training sets of samples and a plurality of testing sets of samples from a data set of clinical records in a time window, the plurality of training sets of samples and the corresponding plurality of testing sets of samples including different samples of the data set;
training a model from the training sets of samples;
evaluating area under the receiver operating characteristic (ROC) curve (AUC) of the model on the testing sets of samples;
repeating the obtaining, the training, and the evaluating to compute coefficients of a plurality of risk factors from all repetitions of the obtaining, the training, and the evaluating which are used to compute p-values and an average AUC of all the repetitions;
determining statistical significance for the plurality of risk factors of the model from the plurality of training sets of samples;
determining a plurality of performance metrics of the model from the plurality of testing sets of samples; and
determining an evaluation metric of the plurality of risk factors for the model based on a coefficient for balancing of the average AUC and the p-values, the statistical significance and the plurality of performance metrics, the evaluation metric being for improving accuracy of the model,
wherein the coefficient favors the plurality of performance metrics by positively weighting and penalizes the p-values by negatively weighting, and
wherein the obtaining the plurality of training sets of samples and the plurality of testing sets of samples comprises:
determining the plurality of training sets of samples by performing a bootstrapping method on the data set; and
determining the plurality of testing sets of samples from samples in the data set that are not in the corresponding plurality of training sets of samples,
further comprising
obtaining a second plurality of training sets of samples and a second plurality of testing sets of samples from the data set, the second plurality of training sets of samples and the corresponding second plurality of testing sets of samples including different samples of the data set;
determining a second statistical significance for a second plurality-of risk factors of a model from the second plurality of training sets of samples;
determining a second plurality of performance metrics of the model from the second plurality of testing sets of samples;
determining a second evaluation metric of the second plurality of risk factors for the model based on the second statistical significance and the plurality of performance metrics; and
determining one of the plurality of risk factors and the second plurality of risk factors as optimal risk factors based on the evaluation metric and the second evaluation metric,
wherein the determining the statistical significance for the plurality of risk factors comprises:
determining the plurality of coefficients for the plurality of risk factors from the plurality of training sets of samples; and
determining a plurality of values indicating the statistical significance for the plurality of risk factors based on the plurality of coefficients.

2. The computer-implemented method of claim 1, wherein the determining the plurality of values indicating the statistical significance for the plurality of risk factors based on the plurality of coefficients comprises:
determining means and standard errors of the plurality of coefficients for the plurality of risk factors; and
determining the plurality of p-values based on the means and standard errors of the plurality of coefficients.

3. The computer-implemented method of claim 1, wherein the p-values are computed by a z-test.

4. The computer-implemented method of claim 1, embodied in a cloud-computing environment.

5. A system comprising:
a processor; and
a memory, the memory storing instructions to cause the processor to perform:
obtaining a plurality of training sets of samples and a plurality of testing sets of samples from a data set of clinical records in a time window, the plurality of training sets of samples and the corresponding plurality of testing sets of samples including different samples of the data set;
training a model froth the training sets of samples;
evaluating area under the receiver operating characteristic (ROC) curve (AUC) of the model on the testing sets of samples;
repeating the obtaining, the training, and the evaluating to compute coefficients of a plurality of risk factors from all repetitions of the obtaining, the training, and the evaluating which are used to compute p-values and an average AUC of all the repetitions;
determining statistical significance for the plurality of risk factors of the model from the plurality of training sets of samples;
determining a plurality of performance metrics of the model from the plurality of testing sets of samples; and
determining an evaluation metric of the plurality of risk factors for the model based on a coefficient for balancing of the average AUC and the p—values, the statistical significance and the plurality of performance metrics, the evaluation metric being for improving accuracy of the model, wherein the coefficient favors the plurality of performance metrics by positively weighting and penalizes the p-values by negatively weighting, and wherein the obtaining the plurality of training sets of samples and the plurality of testing sets of samples comprises:

determining the plurality of training sets of samples by performing a bootstrapping method on the data set; and determining the plurality of testing sets of samples from samples in the data set that are not in the corresponding plurality of training sets of samples, further comprising:

obtaining a second plurality of training sets of samples and a second plurality of testing sets of samples from the data set, the second plurality of training sets of samples and the corresponding second plurality of testing sets of samples including different samples of the data set;

determining a second statistical significance for a second plurality of risk factors of a model from the second plurality of training sets of samples;

determining a second plurality of performance metrics of the model from the second plurality of testing, sets of samples;

determining a second evaluation metric of the second plurality of risk factors for the model based on the second statistical significance and the plurality of performance metrics; and determining one of the plurality of risk factors and the secood plurality of risk factor as optimal risk factors based on the evaluation metric and the segnd evaluation metric.

6. The system of claim 5, wherein the determining the statistical significance for the plurality of risk factors comprises:

determining the plurality of coefficients for the plurality of risk factors from the plurality of training sets of samples; and determining a plurality of values indicating the statistical significance for the plurality of risk factors based on the plurality of coefficients.

7. The system of claim 6, wherein the determining the plurality of values indicating the statistical significance for the plurality of risk factors based on the plurality of coefficients comprises:

determining means and standard errors of the plurality of coefficients for the plurality of risk factors; and determining the plurality of p-values based on the means and standard errors of the plurality of coefficients.

8. The system of claim 5, wherein the p-values are computed by a z-test.

9. The system of claim 5, embodied in a cloud-computing environment.

10. A computer program product for risk evaluation, the computer program product comprising a computer-readable storage medium having program instructions embodied therewith, the program instructions being executable by a computer to cause the computer to:

obtaining a plurality of training sets of samples and a plurality of testing sets of samples from a data set of clinical records in a time window, the plurality of training sets of samples and the corresponding plurality of testing sets of samples including different samples of the data set;

training a model from the training sets of samples;

evaluating area under the receiver operating characteristic (ROC) curve (AUC) of the model on the testing sets of samples;

repeating the obtaining, the training, and the evaluating to compute coefficients of a plurality of risk factors from all repetitions of the obtaining, the training, and the evaluating which are used to compute p—values and an average AUC of all the repetitions;

determining statistical significance for the plurality of risk factors of the model from the plurality of training sets of samples;

determining a plurality of performance metrics of the model from the plurality of testing sets of samples; and determining an evaluation metric of the plurality of risk factors for the model based on a coefficient for balancing of the average AUC and the p-values, the statistical significance and the plurality of performance metrics, the evaluation metric being for improving accuracy of the model, wherein the coefficient favors the plurality of performance metrics by positively weighting and penalizes the p—values by negatively weighting, and wherein the obtaining the plurality of training sets of samples and the plurality of testing sets of samples comprises:

determining the plurality of training sets of samples by performing a bootstrapping method on the data set; and determining the plurality of testing sets of samples from samples in the data set that are not in the corresponding plurality of training sets of samples, further comprising:

obtaining a second plurality of training sets of samples and a second plurality of testing sets of samples from the data set, the second plurality of training sets of samples and the corresponding second plurality of testing sets of samples including different samples of the data set;

determining a second statistical significance for a second plurality of risk factors of a model from the second plurality of training sets of samples;

determining a second plurality of performance metrics of the model from the second plurality of testing sets of samples;

determining a second evaluation metric of the second plurality of risk factors for the model based on the second statistical significance and the plurality of performance metrics; and determining one of the plurality of risk factors and the second plurality of risk factors as optimal risk factors based on the evaluation metric and the second evaluation metric.

11. The computer program product of claim 10, wherein the instructions, when executed on the computer, cause the computer to:

determine the plurality of coefficients for the plurality of risk factors from the plurality of training sets of samples; and determine a plurality of values indicating the statistical significance for the plurality of risk factors based on the plurality of coefficients.

12. The computer program product of claim 11, wherein the instructions, when executed on the computer, cause the computer to:

determine means and standard errors of the plurality of coefficients for the plurality of risk factors; and determine the plurality of p-values based on the means and standard errors of the plurality of coefficients.

\* \* \* \* \*